United States Patent [19]

Tsuruo et al.

[11] Patent Number: 5,087,560
[45] Date of Patent: Feb. 11, 1992

[54] MONOCLONAL ANTIBODY FOR USE IN DRUG RESISTANT CANCERS AND PRODUCTION THEREOF

[75] Inventors: Takashi Tsuruo; Hirofumi Hamada; Haruo Sugano, all of Tokyo, Japan

[73] Assignee: Japanese Foundation for Cancer Research, Tokyo, Japan

[21] Appl. No.: 593,276

[22] Filed: Oct. 1, 1990

Related U.S. Application Data

[63] Continuation of Ser. No. 312,336, Feb. 16, 1989, abandoned, which is a continuation of Ser. No. 905,452, Sep. 10, 1986, abandoned.

Foreign Application Priority Data

Sep. 11, 1985 [JP] Japan .................. 60-201445

[51] Int. Cl.$^5$ .......... C12G 1/68; C12P 21/00; C12N 15/00
[52] U.S. Cl. .................. 435/6; 435/70.21; 435/172.2; 435/240.27; 435/103; 435/106; 435/107; 530/387
[58] Field of Search ............ 435/6, 68, 172.2, 240.27; 935/103, 106, 107

[56] References Cited

PUBLICATIONS

Bell et alii. J. Clin. Onc. Rev., vol. 3(3); 311-315 (1985).
Kartner et alii. Science, vol. 221: 1285-1288 (Jul./Sep. 1983).
Young et alii. Prog. Clin. Biol. Res. 1983; pp. 293-304 abstract only.
N. Young et al.., Globin Gene Expression and Hematopoietic Differentiation, pp. 293-304, 1983 Alan R. Liss, Inc., New York, N.Y.
Chem. Abs., vol. 100 (9):443; 6295q (2/27/84).
Chem. Abs.; vol. 104(5): 43; 3285h (2/3/86).
Proc. Natl. Acad. Sci. U.S.A., vol. 83: 7785-7789 (1986).
Kartner, N. et al. Nature vol. 316, Aug. 29, 1985 pp. 820-823.
Galfre, G. & Milstein, C., Methods in Enzymology, 73:3-45, 1981.
Tsuruo, T. et al., Gann, 74:751-758, 1983.
Kearney, F. et al., The Journal of Immunology, 123 (4):1548-1550, 1979.

*Primary Examiner*—Robert A. Wax
*Assistant Examiner*—Bradley L. Sisson
*Attorney, Agent, or Firm*—Finnegan, Henderson, Farabow, Garrett, and Dunner

[57] ABSTRACT

Monoclonal antibodies are disclosed that may be produced by hybridomas obtained by fusing a mouse spleen cell immunized with an ADRIAMYCIN ®-resistant human tumor cell and a mouse myeloma cell and which inhibit selectively the growth of cancer cells possessing pleiotropic drug resistance or enhance their sensitivity to said drug.

4 Claims, 4 Drawing Sheets

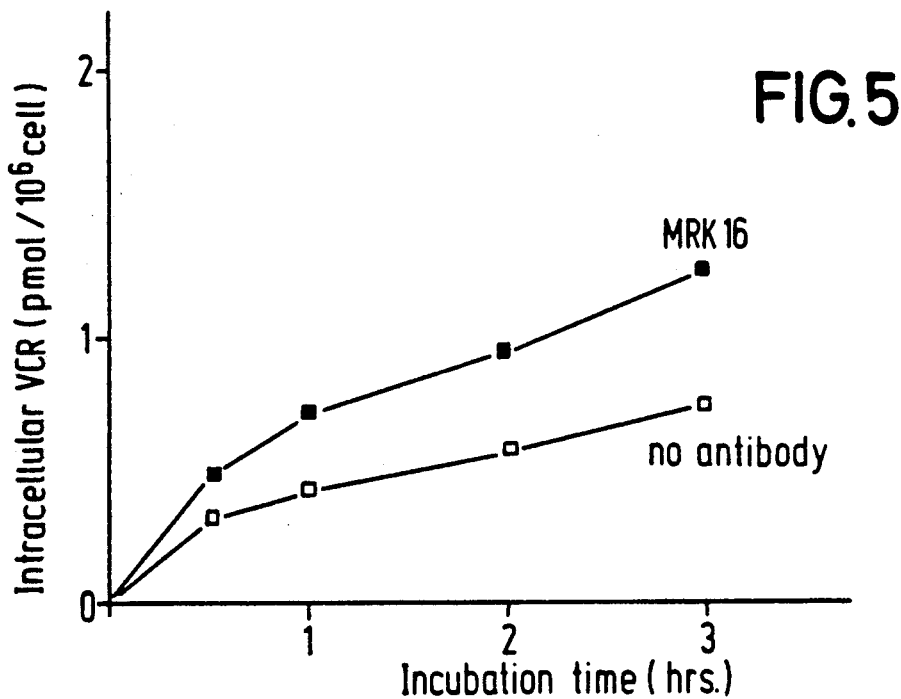
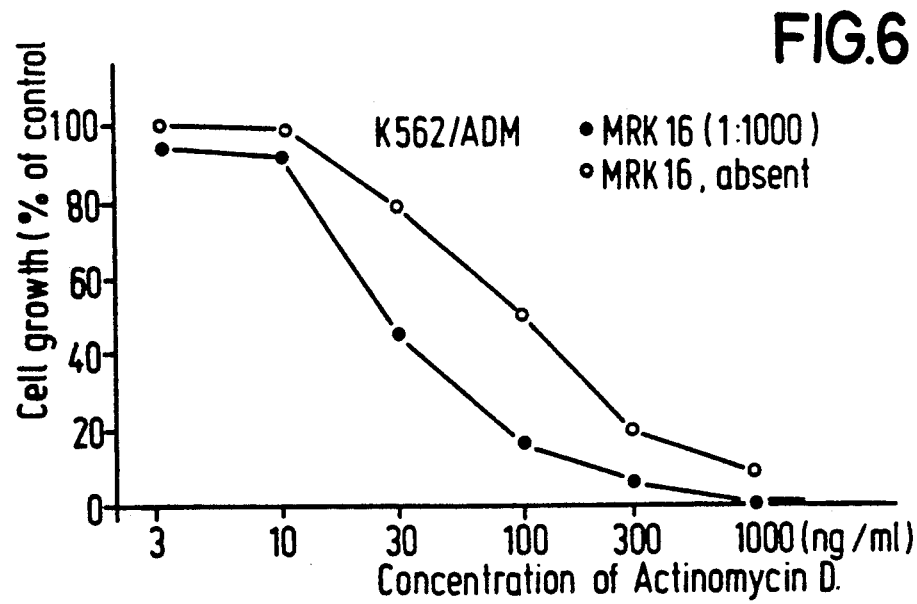

MONOCLONAL ANTIBODY FOR USE IN DRUG RESISTANT CANCERS AND PRODUCTION THEREOF

This application is a continuation of application Ser. No. 07/312,336, filed Feb. 16, 1989, which is a continuation of application Ser. No. 06/905,452, filed Sept. 10, 1986, both of which are now abandoned.

BACKGROUND OF THE INVENTION

1. Technical Field

This invention relates to a monoclonal antibody in relation to drug-resistant cancers and production thereof. More particularly, the present invention relates to the monoclonal antibody, a hybridoma which produces the same and a process for producing the monoclonal antibody.

It has heretofore been observed that cancer cells which are resistant to an antitumor agent selectively appear upon treatment of the cancer by chemotherapy, which poses a serious problem in the art. It may be an approach to overcoming the problem of drug-resistance to increase the dosage of the antitumor agent. However, increase of dosage will give unnecessary pains to patients through the side effects of disorders to normal cells. Another approach to overcoming the problem of drug-resistance may be to use several types of antitumor agents in combination, but this approach can be accompanied by a problem of what is called pleiotropic drug-resistance, thus bringing about little effect in many cases.

Accordingly, for the purpose of overcoming such drug-resistance of cancer cells, it is an important task to establish a drug or a method which has little side effects, high selectivity and effectiveness against cancer cells exhibiting pleiotropic drug resistance.

2. Prior Art

A monoclonal antibody which has selectivity to cancer cells having pleiotropic drug-resistance has been already prepared [J. Clin. Oncology, vol. 3, p. 311~315 (1985)]. It is a monoclonal antibody which is reactive with glycoproteins having molecular weights of 170,000 to 180,000 daltons which appear specifically on the cell membrane of a cancer cell exhibiting pleiotropic drug-resistance. However, the resistant cell line used in preparation of this monoclonal antibody is not derived from human but from Chinese hamster, and also nothing is reported about sensitivity of the drug-resistant cancer cells to the drug when use is made of this monoclonal antibody.

Therefore, nobody in the art would believe that the monoclonal antibody according to this prior art can be used in selective treatment of human drug-resistant cancer cells.

SUMMARY OF THE INVENTION

The present inventors have found that the monoclonal antibody produced by the hybridoma obtained by fusion between a mouse spleen cell immunized with ADRIAMYCIN ®-resistant tumor cell and a mouse myeloma cell inhibits selectively growth of a cancer cell which exhibits peiotropic drug resistance or enhances its sensitivity to the drug.

Accordingly, the monoclonal antibody in relation to drug-resistant cancers is characterized by the definitions (i) to (iv) shown below.

The process for producing the monoclonal antibody in relation to drug-resistant cancers as defined below by (i) to (iv) comprises the steps (a) to (g) shown below.

(i) the monoclonal antibody is produced by a hybridoma which is formed as fusion product between a mouse myeloma cell and a spleen cell from a mouse that has been immunized with an ADRIAMYCIN ®-resistant K562/ADM cell line of a human myelogenous leukemia cell K562;

(ii) the monoclonal antibody is capable of specifically recognizing an ADRIAMYCIN ®-resistant cell line (iii) the antibody is capable of, inhibiting growth of an ADRIAMYCIN ®-resistant cell line or enhancing sensitivity of the cell line to vincristine or actinomycin D; and (iv) the antibody belongs to the IgG isotype.

(a) immunizing, a mouse with an ADRIAMYCIN ®-resistant K562/ADM cell line which has been established from a human myelogenous leukemia cell K562 cell line;

(b) taking spleen cells out of the immunized mouse and preparing a dispersion of the cells;

(c) subjecting the spleen cells together with mouse myeloma cells to cell fusion conditions thereby to prepare a hybridoma as a fusion product between the spleen cell and the myeloma cell;

(d) culturing the mixture of cells obtained from the step (c) on a selective medium on which only the hybridoma can grow;

(e) determining whether the hybridoma-containing supernatant of the medium contains the antibody desired thereby select hybridoma capable of producing the antibody desired;

(f) cloning the hybridoma thus selected; and (g) incubating the clone in an abdominal cavity of a mouse or on a medium thereby to obtain a monoclonal antibody formed and accumulated in the cancerous ascites or the supernatant of the medium.

The present invention also relates to a hybridoma. That is, the hybridoma capable of producing monoclonal antibody according to the present invention is prepared between a spleen cell obtained from a mouse immunized with an ADRIAMYCIN ®-resistant cell line K562/ADM of a human myelogenous leukemia cell K562 cell line and a mouse myeloma cell.

EFFECT

As mentioned above and also apparently seen from the experimental results as described hereinafter, the monoclonal antibody according to the present invention has the ability of selectively inhibiting growth of a cancer cell exhibiting pleiotropic drug-resistance or enhancing its sensitivity to drugs.

Therefore, the monoclonal antibody according to the present invention can be one means for solving the important task of establishing a drug or a method which has little side effects, high selectivity and effectiveness against cancer cells exhibiting pleiotropic drug resistance.

BRIEF DESCRIPTION OF THE DRAWINGS

FIG. 5 is a graph showing uptake of vincristine by MRK16; and

FIG. 6 is a graph showing enhancement of sensitivity to actinomycin D by MRK 16.

DETAILED DESCRIPTION OF THE INVENTION

Figure 1B:
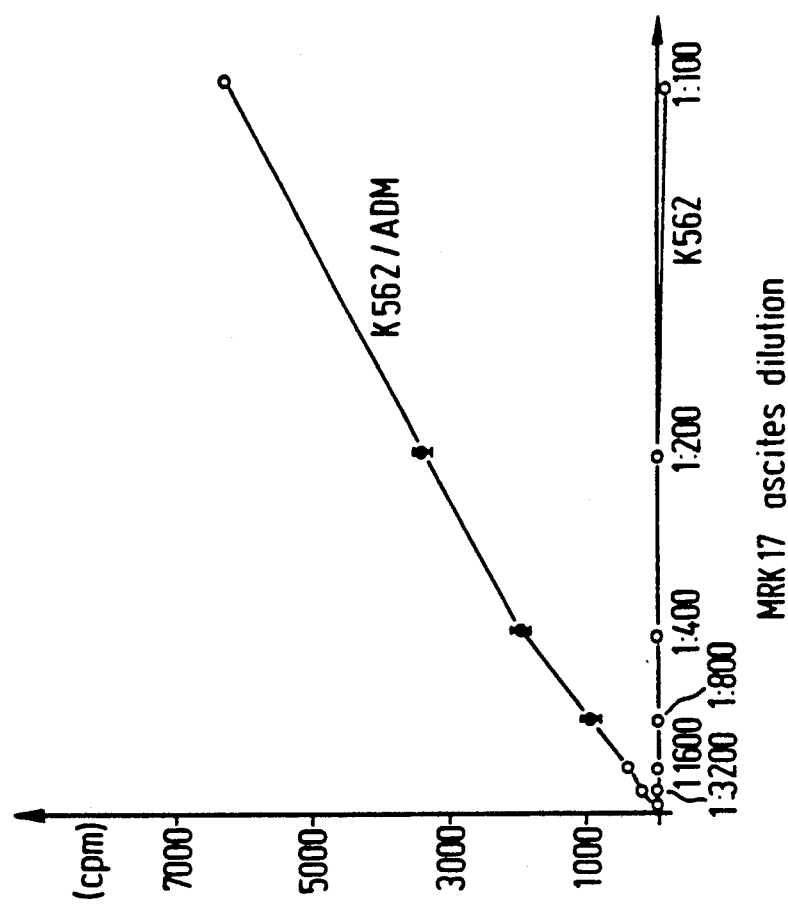
FIGS. 1(A) and (B) are graphs showing reactivities, upon radioimunoassay, of MRK16(A) and MRK17(B) with human myelogenous leukemia cells K562 and its adriamycin-resistant strain of K562 ADM cells.

The monoclonal antibody according to the present invention can be produced according to any desired method suited for the purpose comprising production of a hybridoma by cell fusion and production of a monoclonal antibody by this hybridoma, while bearing in mind that the cell for the antigen is an ADRIAMYCIN ®-resistant human tumor cell.

Concerning production of monoclonal antibody including the cell fusion method, some reviews and textbooks have been already known and therefore reference should be made to those literatures concerning necessary informations other than the description given below about one example of the present invention. Some suitable literatures may be, for example, G. Galfre, C. Milstein: Methods Enzymol., vol. 73, p. 3~46 (1981) and J. W. Goding: Monoclonal Antibodies: Principles and Practice, Academic Press, 1983.

PREPARATION OF HYBRIDOMA/MONOCLONAL ANTIBODY (1) Selection and establishment of ADRIAMYCIN ®-resistant cancer cell:

The present inventors have already selected and established a cell line of human myeloma cell (K562/VCR), resistant to vincristine which is a vincaalkaloid type antitumor agent. This resistant cell line has already exhibited a light degree of cross-resistance to ADRIAMYCIN ® which is an anthracycline type antitumor agent ["Gann", vol. 74, p. 751~758 (1983)]. In the example of the present invention, this cell line is used as the starting cell line. This cell line is freely available from the Foundation, Gann Kenkyukai-Cancer Chemotherapeutical Center (Kamiikebukuro 1-37-1, Toshima-ku, Tokyo, Japan).

First, the vincristine-resistant cell line K562/VCR is cultured in a RPMI1640 (10% fetal calf serum (FCS)) containing 3 nM of ADRIAMYCIN ® which is CI50, and the grown cells are successively cultured in cultural media in which the concentration of ADRIAMYCIN ® is increased stepwise by a ratio of about 3-fold to select a drug-resistant cell line at high concentration.

The drug-resistant cell line selected is grown for about one year under the presence of the drug at the maximum concentration at which the resistant cell line can grow, and thereafter stable cell lines which will no longer lose the resistant properties even when cultured in a medium containing no drug are obtained.

(2) Preparation of immunized animal spleen cell:

The ADRIAMYCIN ®-resistant human myelogenous leukemia cell K562/ADM strain obtained is once washed with 0.5 ml of Hanks' balance buffer saline (hereinafter called HBBS) to $10^7$ cells per one mouse, and then suspended in the same amount of HBBS and administered intraperitoneally into a female Balb/c mouse of 4 to 6 weeks old. Administration is continued similarly at the rate of once per week until the antibody valve rises sufficiently, and three days before cell fusion, $10^6$ cells suspended in 0.1 ml are administered intravenously as the booster. From the immunized animal thus obtained, the spleen is collected aseptically. The spleen taken out is loosened aseptically on a laboratory dish by means of a pair of tweezers, and the number of cells obtained is calculated by sampling a part thereof.

For assaying of antibody value, the anti-ADRIAMYCIN ®-resistant cell line antibody value is examined by enzyme immunoassay according to the solid phase method as described below.

① Pretreatment of plate: on Falcon plate 3912, 50 μl of 0.001% poly-L-lysine solution is added per well and after incubation at room temperature for 30 minutes, water is drained, followed by drying on air.

② Binding of cell to plate: 562 parent cell line and K562/ADM resistant cell line are each suspended at a concentration of 2,000,000 cells/ml and apportioned each in 50 μl (100,000 cells) into the respective well, and the cells are bound to the well by centrifugation at 1000 rpm for 5 minutes. Then, binding is made more perfect by addition of 50 μl of 0.5% glutalaldehyde per well.

③ Blocking: for masking of superfluous binding groups, 200 μl of bovine serum albumin (BSA) dissolved to 3% in RPMI1640 was added per well and the treatment is carried out at room temperature for 30 minutes.

④ Addition of sample to be assayed: each 50 μl of the sample for assay of antibody value is added to one well, and K562 and K562/ADM are added respectively for one kind of sample, and incubation is performed at room temperature or 37° C. for 2 hours. Then, washing is repeated 4 times with phosphate buffer saline (PBS).

⑤ Addition of secondary antibody: as the secondary antibody, F (ab')₂ fragment of the peroxidase bound-antimouse Ig antibody of goat [produced by Cappel Co., U.S.A.], which is diluted into a solution to 1,500-fold in PBS, is added into each well and incubation is further performed at room temperature for 2 hours.

⑥ Judgement: as the substrate for peroxidase, o-phenylenediamine is added to each well and after termination of the reaction with sulfuric acid, presence of and difference in color formation between K562 and K562/ADM are judged with naked eyes or an autoreader.

(3) Preparation of mouse myeloma cell:

As the myeloma cell line, for example, 8-azaguanine-resistant myeloma cell line P3-X63-Ag8-653 derived from mouse [Journal of Immunology, vol. 123, p. 1548~1550 (1979)] is used. On the day of fusion, $2 \times 10^7$ or more cells should be ready for use. This cell line is registered as CRL-1580 at American Type Culture Collection (Maryland, U.S.A.) and is freely available therefrom or from Flow Laboratory Inc., U.S.A.

(4) Cell fusion:

The spleen cell obtained from the immunized animal in (2) and the myeloma cell obtained in (3) are mixed so that the number of cells may be spleen cell: myeloma cell = 7:1, and cell fusion is effected in a RPMI-1640 medium containing 43% of polyethyleneglycol 4000 and 13% of dimethylsulfoxide.

The fused cell is grown on a 96-well plastic plate in a RPMI-1640 medium containing hypoxantine; aminopterin and thymidine (hereinafter abbreviated as HAT) for 7 days, and further in a medium containing no HAT.

During this cultivation, the medium is exchanged with new one every 3 to 5 days.

About two weeks after fusion, an examination is carried out for the cells survived thereby to check the presence of antibody capable of binding selectively to K562/ADM in the culture supernatant, according to the enzyme immunoassay shown in the above (2).

For positive wells, cloning of positive cells is performed by repeating the limiting dilution method with the use of a RPMI-1640 containing 20% fetal calf serum as the diluting solution.

(5) preparation of monoclonal antibody:

To a mouse which has been previously pretreated by administering intraperitoneally 0.5 ml of pristan per mouse, $10^7$ hybridoma cells producing the desired antibody are administered intraperitoneally. Then ascites tumors of the hyberdoma occur about two weeks after administration, and the ascites build up is collected and the presence of the antibodies accumulated is examined by the enzyme immunoassay of the above (2).

When the ascites cells are to be stored, the supernatant after centrifugal separation is divided into small aliquots and stored under freezing at $-70°$ C.

For further purification of the antibody, the ascite is salted out at 4° C. with 45% saturated ammonium sulfate, followed further by gel filtration by use of Sephacryl-400 (Pharmacia Co., Sweden). Quantitative determination of protein is carried out by the Rowry method.

PROPERTIES OF MONOCLONAL ANTIBODY

The class of the monoclonal antibody obtained as described above can be judged by use of the antibodies of the respective classes of antimouse Ig of rabbit (produced by Cappel Co., U.S.A.).

On the other hand, local existence of the antigen in cell can be known by observation of fluorescence under a microscope by use of a goat antimouse Ig antibody bound with FITC which is the fluorescent chromogenic group (produced by Cappel Co., U.S.A.).

Selectivity for K562/ADM of drug-resistant cell line can be examined according to the enzyme immunoassay of the above (2) with the use of the parent cell line K562 as a control, or otherwise by measuring the extent of inhibition of cell growth against the respective cell lines. The change of the sensitivity of the drug-resistant cell line to a drug with the monoclonal antibody can be examined also by measuring the extent of inhibition of the cell growth by permitting the cell line to be co-present with the monoclonal antibody in the presence of various concentrations of the drug.

Typical examples of the monoclonal antibodies according to the present invention include isotypes $IgG_3$, $IgG_{2a}$ and $IgG_1$, etc. In the present invention, these are named as MRK4, MRK16 and MRK17, respectively. Among them, those representative are MRK16 and MRK17.

The monoclonal antibodies MRK16 and MRK17 have the activity of selective growth inhibition against drug-resistant human cancer cells or the activity of increasing sensitivity to drugs (see Example II).

EXPERIMENTAL EXAMPLES

EXAMPLE I

Preparation of monoclonal antibody a) Selection, and establishment of ADRIAMYCIN ®-resistant cell line:

For selection of an ADRIAMYCIN ®-resistant cell line K562/ADM, a vincristine-resistant cell line K562/VCR which had been prepared from the same parent cell line of a human myelogenous leukemia cell K562 cell line was used as the starting cell line.

First, K562/VCR was cultured in a RPMI-1640 (containing 10% fetal calf serum) containing 15 nM ADRIAMYCIN ® which is the IC50 (concentration which inhibits 50% of cell growth) for this cell line for one week, and thereafter the cells grown were selected. Next, the drug concentration of ADRIAMYCIN ® was increased to about 3-fold of 50 nM and cultivation was carried out at that concentration for one week. The resistant cells obtained were further cultured at a drug concentration which was increased stepwise to 150 nM which was the 3-fold amount, until finally ADRIAMYCIN ®-resistant cells capable of growing even in the presence of 450 nM of ADRIAMYCIN ® could be obtained.

The ADRIAMYCIN ®-resistant cells were continuously cultured in a medium containing 500 nM of this drug for about one year, whereby they became stable resistant cell lines which would not lose the resistance even when cultured in a medium containing no ADRIAMYCIN ® for about 3 months thereafter. The present inventors named this cell line "K562/ADM".

b) Immunization of mouse and cell fusion:

For the K562/ADM obtained in a), an amount corresponding to $10^7$ cells per mouse was suspended in 0.5 ml of HBBS and, after washing once, administered intraperitoneally into a female Balb/c mouse of 4 to 6 weeks old. Similarly, administration was continuously repeated once per week over 6 weeks and, in the last week, $10^6$ cells as the booster were suspended in 0.1 ml of HBSS and intravenously administered. Three days later, the spleen was aseptically taken out. The spleen cells were obtained in numbers of 1.4 to $3 \times 10^8$ per mouse. The spleen was loosened by a pair of tweezers and made into a suspension.

Cell fusion was practiced following the method of Kohler & Milstein. More specifically, $1.4 \times 10^8$ of the spleen cells were fused with $2 \times 10^7$ of p3-63-Ag8-653 myeloma cells in a RPMI 1640 medium containing 43% polyethyleneglycol 4000 and 13% dimethylsulfoxide.

c) Selection of hybridoma:

After cell fusion, the fused cells were grown in HAT medium on a 96-well plastic plate for 7 days and further in a medium containing no HAT for 7 days. Culturing of about 300 to 400 wells per mouse was conducted and growth of cells could be seen in about 75% of the wells. For the culture supernatant of these wells, the reactivities with K562 and K562/ADM were examined according to enzyme immunoassay. As a result, in about ⅔ of the wells, positive color formations of the same extent could be seen in both of K562 and K562/ADM while no reaction with both occurred in the remaining ⅓ of the wells. Further, wells were found which reacted with 0 to 3 K562 and K562/ADM per 300 to 400 wells derived from one mouse, but apparently reacted more strongly with K562/ADM.

After screening of about 6,000 wells by use of 18 mice in all, 25 wells having the same reactivity of K562<K562/ADM were found.

d) Cloning of hybridoma:

For 25 wells selected in c), the reaction positive cells were cloned according to the limiting dilution method. As the diluting solution, a RPMI-1640 containing 20% fetal calf serum was used and culturing was carried out with dilution so that 0.5 to 5 cells were partitioned per well. For each well, presence and the properties of the antibody in the culture supernatant were examined according to enzyme immunoassay. For strongly positive wells, cloning according to the limiting dilution method was further repeated, whereby clones of 25 stable hybridomas could be obtained.

e) Production and purification of antibody:

For 16 clones of the 25 hybridomas obtained in d), $10^7$/mouse were administered intraperitoneally into mouse to generate ascites cancer, and 5 to 10 ml of ascites cancer cells per mouse were obtained two weeks later. The remaining 9 clones were stored under freezing (at $-70°$ C.). The total protein content in the ascites cells was found to be 5 to 15 mg/ml.

Purification of the antibody was carried out by salting out these ascites with 45% saturated ammonium sulfate, followed by gel filtration with Sephacryl-400 (produced by Pharmacia, Sweden).

EXAMPLE II

Figure 1A:
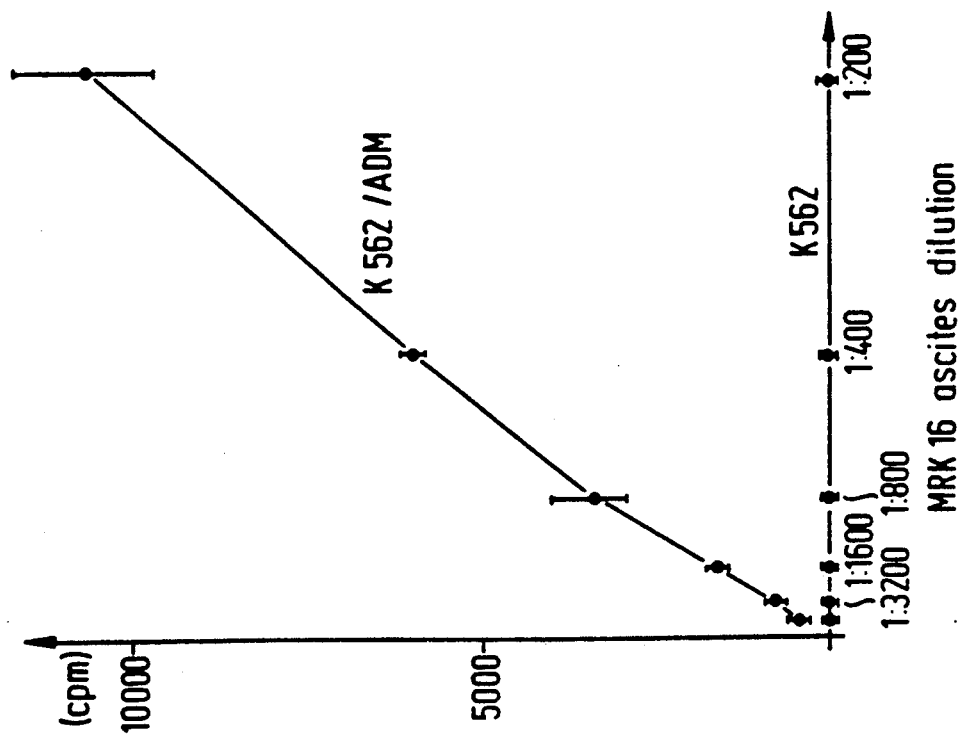
Figure 2B:
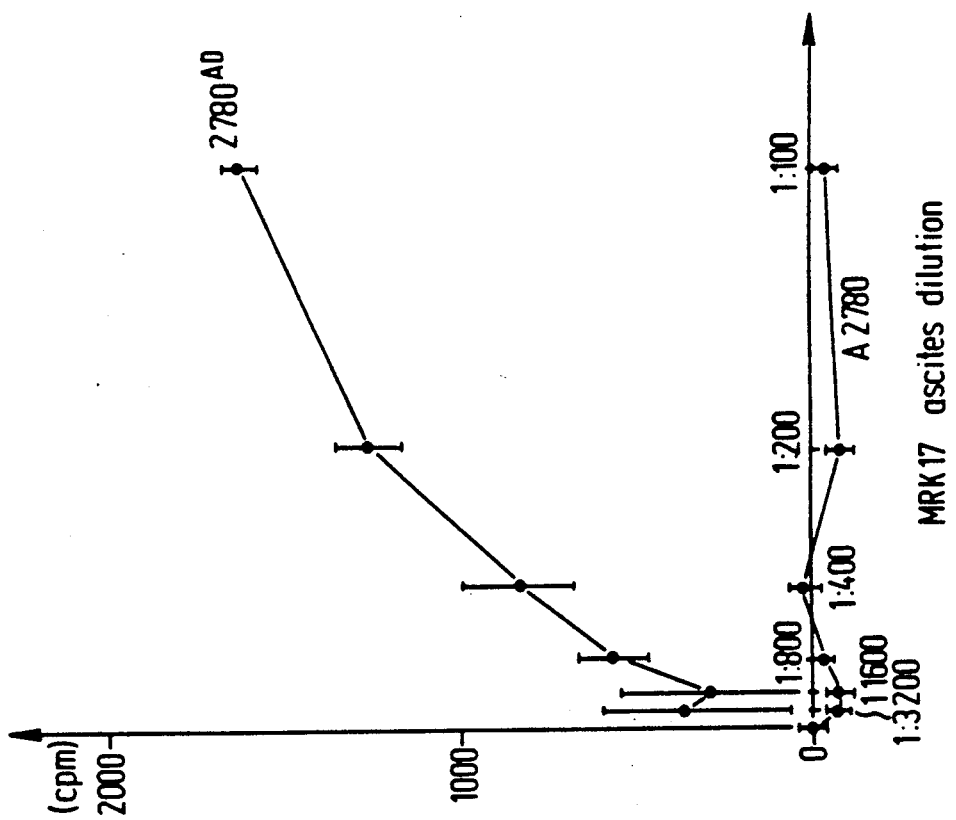
FIGS. 2(A) and (B) are graphs showing reactivities, upon radioimmunoassay, of MRK16(A) and MRK17(B) with human ovary cancer cells 2780 and with the adriamycin-resistant strain of the cells 2780, namely 2780^AD.
Figure 2A:
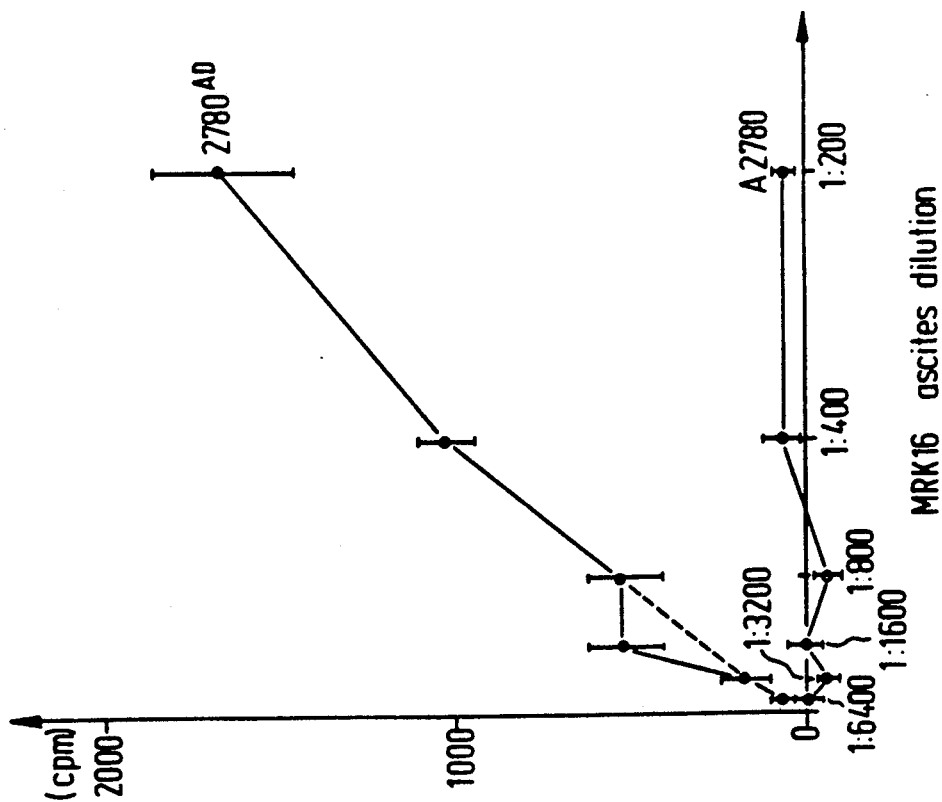
Figure 3:
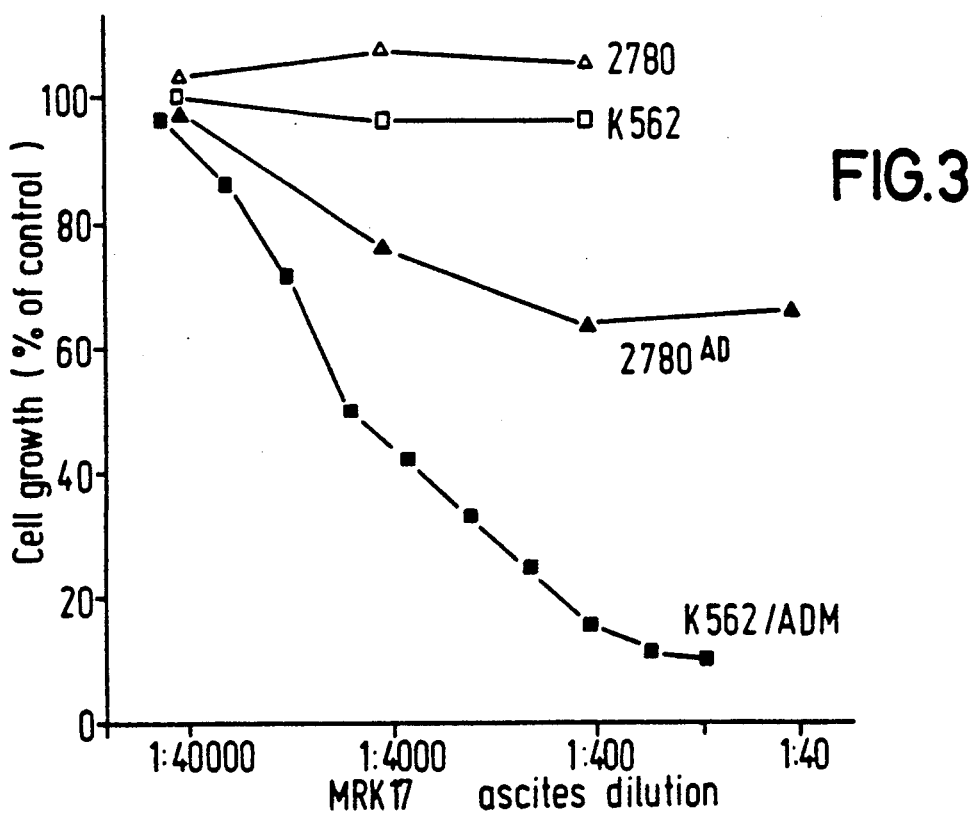
FIG. 3 is a graph showing cell growth inhibition by MRK17.

Properties of monoclonal antibodies MRK16 and MRK17 a) Isotype of antibody:

For the 16 kinds of the monoclonal antibodies obtained, their isotypes were determined by means of a kit using the antibodies of respective isotypes of rabbit anti-mouse Ig produced by Cappel Co., U.S.A. As a result, it was found that one $IgG_3$ (MRK4), one $IgG_{2a}$ (MRK16) and one $IgG_1$ (MRK17) were obtained, all of the others belonging to IgM isotype.

b) Judgement of antigenic site according to the fluorescent antibody method:

By use of FITC-bound goat anti-mouse Ig antibody (Cappel Co.), the binding sites of the respective monoclonal antibodies of MRK16 and MRK17 with the antigen on K562/ADM cell were examined. As a result, in both cases, fluorescent color formation distributed in a ring was observed on cell membrane surface. That is, either one of the antibodies was found to recognize the antigen existing locally on the membrane of the K562/ADM cell. When the same treatment was carried out on the parent cell line of K562 as control, no such fluorescent color formation could be seen at all. Thus, it has been found that both MRK16 and MRK17 have strong selectivities for K562/ADM. Also, according to the radioimmunoassay, it has been found that either MRK16 or MRK17 does not react with K562 cells but reacts with extremely high selectivity with K562/ADM which is the resistant cell line (see FIG. 1). More specifically, $10^6$ cells were allowed to react respectively with ascites diluted solutions of MRK16 and 17 and, after washing the cells, the cells were incubated with F (ab')$_2$ fragment of sheep antimouse Ig labelled with $^{125}$I (produced by Amersham Co., U.K.) at 4° C. for 30 minutes. After washing, the reactivities (cpm) of MRK16 and 17 which had reacted with the cells were measured to obtain the results as shown in FIG. 1.

c) Discrimination of other drug-resistant cell lines:

Heretofore, only a few number of ADRIAMYCIN ®-resistant strains have been found in human tumor cell lines. For the only available ADRIAMYCIN ®-resistant cell-line 2780$^{AD}$ of a human ovary carcinoma cell-line 2780, the reactivities with MRK16 and MRK17 were examined by use of radioimmunoassay. As a result, both of the monoclonal antibodies were found to react more strongly with the resistant cell-line of 2780$^{AD}$ as compared with the parent cell-line of 2780 (see FIG. 2). More specifically, $3 \times 10^5$ cells were put on a dish, and 24 hours later when the cells were already adhered onto the dish, and the reactivities (cpm) of MRK16 and 17 were measured similarly as in the case shown in FIG. 1 to obtain the results as shown in FIG. 2.

d) Selective cell growth inhibition of MRK17 against K562/ADM:

For the resistant cell line K562/ADM and its parent cell line K562, and also for the resistant cell line 2780$^{AD}$ belonging to another cell line and its parent cell line 2780 for comparative purpose, an ascites containing the monoclonal antibody MRK17 was diluted stepwise for examination of the inhibitory effect against cell growth, respectively (see FIG. 3). More specifically, $2 \times 10^4$ K562 and K562/ADM cells, and $6 \times 10^4$ 2780 and 2780$^{AD}$ cells were incubated together with the ascites diluted solution of MRK17, and the cell number after 72 hours was measured and the percent growth inhibitions calculated therefrom to obtain the results as shown in FIG. 3.

As a result, it was found that substantially no inhibition could be seen against the respective sensitive parent cell lines of K562 or 2780 even when the concentration of the antibody was increased to dilution of 1/400, while about 30% growth inhibition could be seen in the drug-resistant cell line of 2780$^{AD}$ at the same antibody concentration, and 80% growth inhibition with K562/ADM, and even 90% or higher growth inhibition at the diluted antibody of 1/100 in the case of K562/ADM were observed. (triplicate data SD<4%)

When the same test was conducted by use of MRK16, a light degree of growth inhibition of about 12% at the maximum could be seen against K562/ADM.

Figure 4:
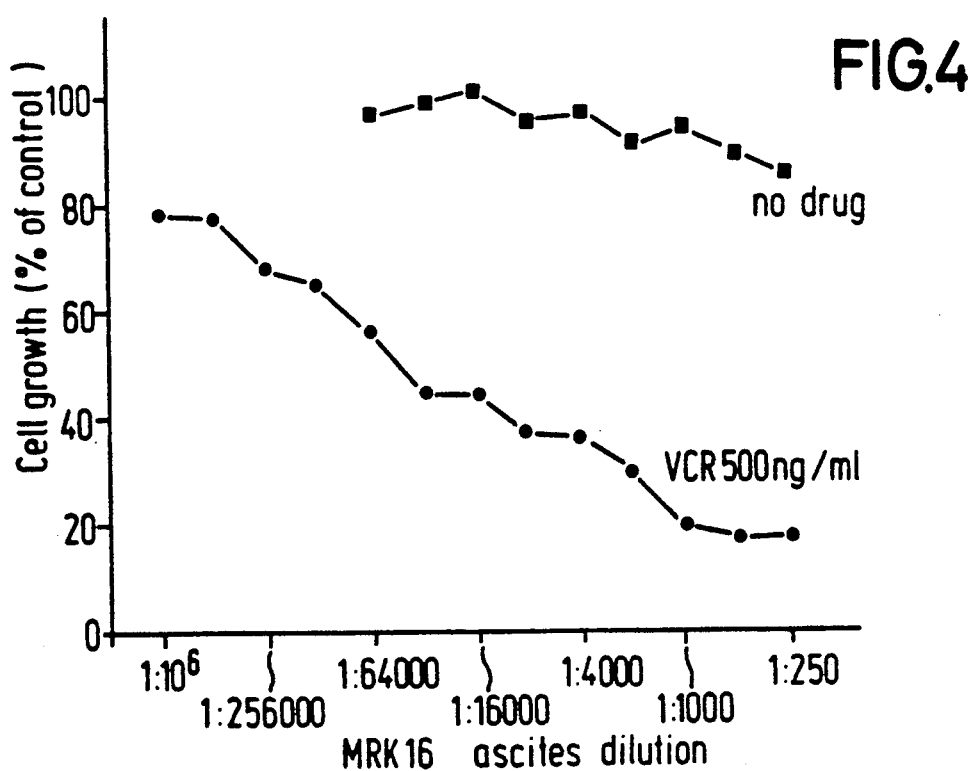
FIG. 4 is a graph showing cell growth inhibition by a combination of MRK16 and vincristine.

Thus, the great characteristic feature of MRK17 can be said to have a potent and selective growth inhibition activity for drug-resistant cell lines.

e) Effect on drug-sensitivity of K562/ADM by MRK16:

In the above d), MRK16 was found to have a light degree of direct growth inhibition effect against the drug-resistant cell line K562/ADM When vincristine was added at a concentration of 0.5 μg/ml to this experiment ratio, however, growth inhibition against the resistant cell line up to about 75% at the maximum was observed by the co-presence of MRK16 (see FIG. 4). More specifically, $2 \times 10^4$ K562/ADM cells either in the presence or absence of 500 ng/ml of vincristine (VCR) were incubated together with ascites diluted solutions of MRK16, and the growth inhibition percents after 72 hours were measured to obtain the results as shown in FIG. 4.

When the effect of MRK16 for accumulation in K562/VCR cells by use of vincristine was examined, an increase by about 60 to 70% as compared with the control test without addition of the antibody could be seen (see FIG. 5). More specifically, $2 \times 10^5$ K562/VCR cells either in the presence or absence of MRK16 (ascites diluted to 1:200) were incubated together with [$^3$H] VCR (100 nM) and the vincristine incorporated within the cell was quantitated to obtain the results as shown in FIG. 5.

Thus, MRK16 has the possibility of recognizing the acting site which participates in expelling intracellular drugs out of the cells which are more advanced in resistant cell lines.

Here, when the change in sensitivity to vincristine was examined by use of 2780$^{AD}$ which is a resistant cell line other than K562/ADM, reduction by 20 to 30% in terms of IC50 value, namely increase of sensitivity to the drug could be seen.

Also, other than vincristine, MRK16 could potentiate the sensitivity of K562/ADM to actinomycin D by about 3-fold (see FIG. 6). More specifically, $2 \times 10^4$ K562/ADM cells either in the presence or absence of MRK16 (ascites diluted to 1:1000) were incubated at 37° C. together with various concentrations of actinomycin D, and the growth inhibitory percents after 72 hours were measured to obtain the results as shown in FIG. 6.

From these results, it can be said that MRK16 can act selectively on a large number of anti-cancer drug-resistant cell lines to enhance sensitivity to the drug.

We claim:

1. A hybridoma capable of producing a monoclonal antibody, which hybridoma is formed as a fusion product between a mouse myeloma cell and a spleen cell from a mouse that has been immunized with a doxorubicin-resistant K562/ADM cell line of a human myelogenous leukemia cell K562.

2. The hybridoma as claimed in claim 1 which is hybridoma MRK16 or hybridoma MRK17.

3. A monoclonal antibody for treatment of drug-resistant cancers wherein:
   (a) the monoclonal antibody is produced by a hybridoma which is formed as a fusion product from a mouse myeloma cell and a spleen cell from a mouse which has been immunized with a doxorubicin-resistant K562/ADM cell line of a human myelogenous leukemia cell K562;
   (b) the monoclonal antibody is capable of specifically recognizing an epitope located on the outside of a doxorubicin-resistant cancer cell membrane;
   (c) the antibody is capable of inhibiting growth of doxorubicin-resistant cells or enhancing sensitivity of the cells to vincristine or actinomycin D; and
   (d) the antibody belongs to the IgG isotype.

4. The monoclonal antibodies secreted by hybridomas MRK16 or MRK17.